United States Patent [19]
Brown et al.

[11] Patent Number: 6,071,305
[45] Date of Patent: Jun. 6, 2000

[54] DIRECTIONAL DRUG DELIVERY STENT AND METHOD OF USE

[75] Inventors: James E. Brown, Los Gatos; Wouter E. Roorda, Newark, both of Calif.

[73] Assignee: Alza Corporation, Del.

[21] Appl. No.: 08/976,725

[22] Filed: Nov. 24, 1997

Related U.S. Application Data

[60] Provisional application No. 60/031,471, Nov. 25, 1996.

[51] Int. Cl.[7] .................................................. A61F 2/06
[52] U.S. Cl. ................................ 623/1; 623/12; 606/198; 606/191
[58] Field of Search ...................... 623/1, 12; 604/891.1, 604/892.1; 606/198, 191

[56] References Cited

U.S. PATENT DOCUMENTS

| | | |
|---|---|---|
| 3,797,485 | 3/1974 | Urquhart . |
| 4,203,442 | 5/1980 | Micheals . |
| 4,307,723 | 12/1981 | Finney ...................................... 128/349 |
| 4,309,776 | 1/1982 | Berguer . |
| 4,479,796 | 10/1984 | Kallok . |
| 4,813,925 | 3/1989 | Anderson, Jr. et al. ..................... 604/8 |
| 5,002,661 | 3/1991 | Chick et al. . |
| 5,062,829 | 11/1991 | Pryor et al. . |
| 5,180,366 | 1/1993 | Woods . |
| 5,201,778 | 4/1993 | Brotzu et al. . |
| 5,234,456 | 8/1993 | Silvestrini . |
| 5,246,445 | 9/1993 | Yachia et al. ............................. 606/108 |
| 5,282,823 | 2/1994 | Schwartz et al. . |
| 5,295,962 | 3/1994 | Crocker et al. . |
| 5,304,121 | 4/1994 | Sahatjian . |
| 5,342,348 | 8/1994 | Kaplan . |
| 5,383,927 | 1/1995 | De Goiocoechea et al. . |
| 5,383,928 | 1/1995 | Scott et al. . |
| 5,421,826 | 6/1995 | Crocker et al. . |
| 5,423,885 | 6/1995 | Williams . |
| 5,429,634 | 7/1995 | Narciso, Jr. . |
| 5,441,515 | 8/1995 | Khosravi et al. . |
| 5,443,458 | 8/1995 | Eury . |
| 5,443,496 | 8/1995 | Schwartz et al. . |
| 5,449,382 | 9/1995 | Dayton . |
| 5,464,450 | 11/1995 | Buscemi et al. . |
| 5,500,013 | 3/1996 | Buscemi et al. . |
| 5,578,073 | 11/1996 | Haimovich et al. ......................... 623/1 |
| 5,624,411 | 4/1997 | Tuch ........................................... 623/1 |
| 5,795,591 | 8/1998 | Lee et al. ................................. 424/473 |
| 5,827,538 | 10/1998 | Cusler et al. ............................ 424/473 |
| 5,843,172 | 12/1998 | Yan ............................................. 623/1 |
| 5,897,587 | 4/1999 | Martakos et al. ........................... 623/1 |

FOREIGN PATENT DOCUMENTS

| | | |
|---|---|---|
| 0578998A1 | 1/1994 | European Pat. Off. . |
| 0706784A1 | 4/1996 | European Pat. Off. . |
| 96/26682 | 9/1996 | WIPO . |
| WO 96/26682 | 9/1996 | WIPO ............................... A61F 2/06 |

*Primary Examiner*—David H. Willse
*Assistant Examiner*—Suzette J. Jackson
*Attorney, Agent, or Firm*—Burns, Doane, Swecker & Mathis, L.L.P.

[57] ABSTRACT

The invention relates to a directional drug delivery stent which includes an elongated or tubular member having a cavity containing a biologically active agent. In one embodiment, the active agent is diffused from the reservoir directly to the walls of a body lumen, such as a blood vessel, through directional delivery openings arranged on an outer surface of the elongated member. Another variation of the stent includes an osmotic engine assembly for controlling the delivery of the active agent from the reservoir. The drugs which may be applied by the directional delivery stent include, but are not limited to, steroids, anti-inflammatory agents, restenosis preventing drugs, anti-thrombotic drugs, and tissue growth regulating drugs. The invention also relates to a method of using the directional drug delivery stent.

21 Claims, 8 Drawing Sheets

DIRECTIONAL DRUG DELIVERY STENT AND METHOD OF USE

CROSS REFERENCE TO RELATED APPLICATIONS

This application claims the benefit of U.S. Provisional Application No. 60/031,471, filed Nov. 25, 1996, pursuant to 35 U.S.C. § 119(e).

BACKGROUND OF THE INVENTION

1. Field of the Invention

The present invention relates to a device and method for the directional delivery of a biologically active agent. More particularly, the invention relates to a stent made from an elongated member which has a cavity or interior containing an active agent for sustained directional delivery to a predetermined location in a body lumen, such as the wall of the body lumen.

2. Description of the Related Art

Many diseases cause body lumens to undergo stenosis or a narrowing of a canal within the body. Arteriosclerosis refers generally to a group of diseases in which the lumen of a blood vessel becomes narrowed or blocked, which may prevent a sufficient amount of blood from flowing through the blood vessel to the tissue. This shortage of blood flow caused by arteriosclerosis ultimately can permanently damage tissue and organs.

The therapeutic alternatives available for treatment of arteriosclerotic diseases include dilation of the artery using a pharmaceutical, surgical intervention to remove the blockage, replacement of the blocked segment with a new segment of artery, or the use of a catheter-mounted device such as a balloon catheter to dilate the artery. The dilation of an artery with a balloon catheter is called percutaneous transluminal angioplasty. During angioplasty, a balloon catheter in a deflated state is inserted within a stenotic segment of a blood vessel and is inflated and deflated a number of times to expand the vessel. Due to the inflation of the balloon catheter, the plaque formed on the vessel walls cracks and the vessel expands to allow increased blood flow through the vessel.

Often angioplasty permanently opens previously occluded blood vessels; however, restenosis, thrombosis, or vessel collapse may occur following angioplasty. Restenosis refers to the re-narrowing of an artery after an initially successful angioplasty due to exaggerated healing which causes a proliferation of tissue in the angioplasty area. Thrombosis is a clotting within a blood vessel which may cause infarction of tissues supplied by the blood vessel. In order to prevent restenosis and vessel collapse, stents of various configurations have been used to hold the lumen of a blood vessel open following angioplasty. However, stents do not entirely reduce the occurrence of thrombotic abrupt closure due to clotting; stents with rough surfaces exposed to blood flow may actually increase thrombosis, and restenosis may still occur because tissue may grow through and around the lattice of the stent. To prevent restenosis and thrombosis in the area where angioplasty has been performed, antithrombic agents and other biologically active agents can be employed.

Several stents exist which attempt to deliver active agents to the area in which angioplasty was performed. Some of these stents are biodegradable stents which have been impregnated with active agents. Examples of such impregnated stents are those disclosed in U.S. Pat. Nos. 5,500,013; 5,429,634; and 5,443,458. Other known agent delivery stents include a stent disclosed in U.S. Pat. No. 5,342,348 which includes a biologically active agent impregnated in delivery matrix filaments which may be woven into a stent or laminated onto a stent. U.S. Pat. No. 5,234,456 discloses a hydrophilic stent which can include a biologically active agent disposed within the hydrophilic material of the stent.

Other biologically active agent delivery stents are disclosed in U.S. Pat. Nos. 5,201,778; 5,282,823; 5,383,927; 5,383,928; 5,423,885; 5,441,515; 5,443,496; 5,449,382; 4,464,450; and European Patent Application No. 0 528 039. Other active agent delivery devices are disclosed in U.S. Pat. Nos. 3,797,485; 4,203,442; 4,309,776; 4,479,796; 5,002,661; 5,062,829; 5,180,366; 5,295,962; 5,304,121; 5,421,826; and International Application No. WO 94/18906.

Although known biologically active agent delivery stents deliver a biologically active agent to the area in which angioplasty was performed, they do not directionally deliver the active agent and, consequently, much of the biologically active agent is directed into the blood stream and does not reach the blood vessel wall where treatment is needed. Furthermore, these known agent delivery stents may actually increase the possibility of thrombosis. For example, some current stents attempt to reduce the risk of thrombosis by incorporating an extremely smooth and electropolished surface on the stent. However, this surface is ineffective against thrombosis when such stents are coated with a polymeric drug delivery system that is exposed to the bloodstream; the presence of such polymer drug delivery systems on current stents in the path of the bloodstream may actually initiate clotting.

The previously described problems associated with non-directional beneficial agent delivery provided by current agent delivery stents limits their range of effective use. Because of the above identified constraints of current delivery stents, it is very difficult to administer biologically active agents directionally to a desired area of a body lumen. As described above, delivering a biologically active agent to the walls of a blood vessel is problematic because non-directional delivery of the agent using current delivery stents results in much of the agent being carried away with the blood stream. The previously described constraints of current agent delivery stents has created a need for a solution.

SUMMARY OF THE INVENTION

The device according to the present invention addresses the disadvantages of the prior art by providing a directional delivery stent for delivering a biologically active agent. The stent according to the present invention includes a cavity or interior for containing the biologically active agent which is directionally delivered directly to a desired area of a body lumen, such as the wall of a blood vessel.

According to one aspect of the present invention, a biologically active agent delivery stent is nonbiodegradable and expandable for supporting a body lumen. The stent has an elongated member which has a center line extending along the elongated member. The center line of the elongated member is located radially spaced from the longitudinal center axis of the stent. At least one cavity is formed within the main body of the elongated member for containing at least one biologically active agent, and delivery means are located in only a portion of the circumference of the elongated member for directionally delivering the at least one biologically active agent from the cavity to an exterior of the elongated member.

According to another aspect of the present invention, the elongated member of the directional delivery stent includes an outer surface having a luminal portion and a support portion. The support portion of the outer surface is for supporting a wall of the body lumen. The delivery means directionally delivers the biologically active agent from the cavity through only one of the luminal portion and the support portion.

According to another aspect of the present invention, the nonbiodegradable and expandable stent for supporting a body lumen has a longitudinal axis. The stent includes at least one tubular member having a center axis not coincident with the longitudinal axis of the stent. The tubular member has an interior for containing the at least one biologically active agent, and at least one fluid opening in only a portion of a circumference of the tubular member such that the biologically active agent may be delivered from the interior to a predetermined location.

According to another aspect of the present invention, the directional drug delivery stent includes an osmotic agent provided within the elongated or tubular member for osmotically delivering the biologically active agent.

According to a further aspect of the present invention, the biologically active agent is contained within a delivery matrix located within the cavity or interior.

According to a further aspect of the present invention, a method of directionally delivering a biologically active agent from a nonbiodegradable and expandable stent for supporting a body lumen and having a longitudinal axis, the stent including at least one tubular member having a center axis not coincident with a longitudinal axis of the stent, includes the steps of positioning the stent within a body lumen, and delivering the active agent from a cavity in a tubular member through at least one fluid opening in only a portion of a circumference of the tubular member such that the active agent is delivered to a predetermined location.

According to a further aspect of the present invention, a nonbiodegradable and expandable stent for directionally delivering an active agent includes a nonbiodegradable tubular member that has an exterior surface and an interior surface together defining a tubular member thickness of the tubular member. The tubular member has a recessed active agent receiving portion formed in the exterior surface. The recessed active agent receiving portion has a depth less than the tubular member thickness. The recessed active agent receiving portion contains at least one active agent.

According to a further aspect of the present invention, a method of manufacturing a nonbiodegradable stent includes the steps of: providing a nonbiodegradable tubular member having an exterior surface and an interior surface together defining a tubular member thickness of the tubular member; forming a recessed active agent receiving portion in the exterior surface of the tubular member, the recessed active agent receiving portion having a depth less than the tubular member thickness; and positioning an active agent in the recessed active agent receiving portion.

BRIEF DESCRIPTION OF THE DRAWINGS

The invention will be described in greater detail with reference to the accompanying drawings in which like elements bear like reference numerals, and wherein.

DESCRIPTION OF THE PREFERRED EMBODIMENTS

One aspect of the present invention relates to a directional drug delivery stent 11 including a cavity 20 containing a biologically active agent for directional application. For example, active agents may be directionally applied by diffusion to prevent restenosis, thrombosis, inflammation, to encourage healing, and/or to provide numerous other treatments.

The term "active agent" as used herein is intended to include one or more biologically active agents in combination with pharmaceutically acceptable carriers and, optionally, additional ingredients such as antioxidants, stabilizing agents, permeation enhancers, and the like.

The active agents which may be applied by the present invention generally belong to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of active agents which may be used in the present invention include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

The active agents may be anhydrous or aqueous solutions, suspensions or complexes with pharmaceutically acceptable vehicles, or carriers such that a biologically active amount of agent is delivered. Agent formulations that may be stored for long periods on the shelf or under refrigeration are preferred. The active agents may include pharmaceutically acceptable carriers and additional inert ingredients. In addition, more than one active agent may be incorporated into a formulation for delivery by the stent according to the present invention.

Figure 1:
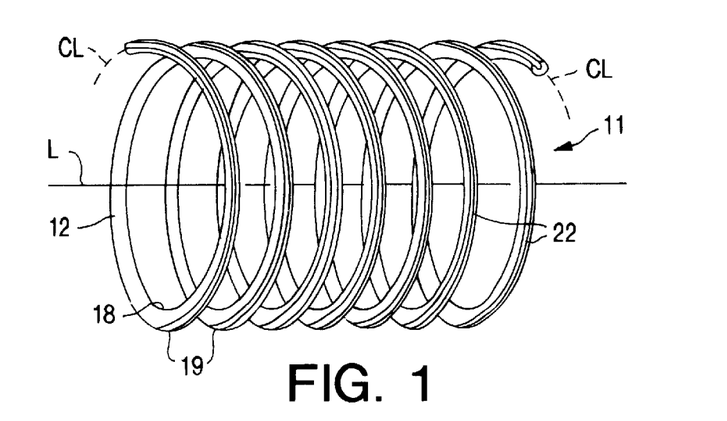
FIG. 1 is a perspective view of a stent according to the present invention.

The directional drug delivery stent 11 according to one embodiment of the present invention illustrated in FIG. 1 is formed from an elongated or tubular member 12. The embodiment of the directional drug delivery stent according to the present invention illustrated in FIGS. 1 and 2 is in the shape of a coil or helix, and is expanded within a body lumen by any known method such as by inflation of a balloon catheter or by heating of shape memory materials.

Figures 2, 2A:
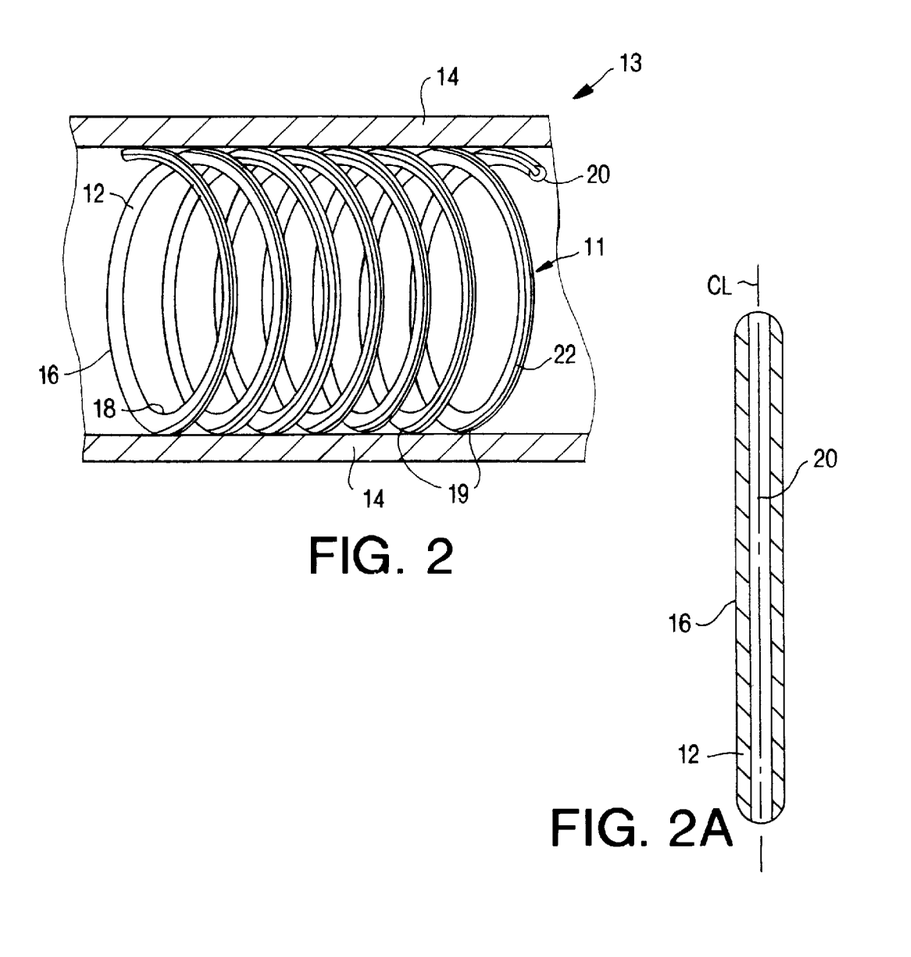
FIG. 2 is a cross sectional side view of a body lumen and a perspective view of a stent according to the present invention located therein.
FIG. 2A is an enlarged sectional view of a portion of the stent of FIG. 2.

The tubular or elongated member 12 of the directional drug delivery stent 11 which is illustrated in FIGS. 1, 2 and 2A is formed with an interior or cavity 20, which according to the embodiment of the present invention illustrated in FIGS. 2, and 2A, is a concave groove within the interior of the elongated member 12, and extending along the entire length of the elongated member. Although the cavity 20 illustrated in FIG. 2 is a concave groove, the interior may be other configurations and need not extend the entire length of the elongated or tubular member 12.

The elongated member 12 of the directional drug delivery stent according to the present invention illustrated in FIGS. 1 and 2 has a center line or center axis CL that runs along the length of the elongated member, such that it follows the path of the elongated member. Thus, if the elongated member 12, which forms the directional drug delivery stent 11 of the embodiment of the present invention illustrated in FIGS. 1 and 2, is in a coil shape, the center line or center axis CL of the elongated member also is in the shape of a coil.

The elongated member 12 of the present invention illustrated in FIGS. 1 and 2 is elongated, such as a strand, filament or fiber, and preferably has a cross section that is circular. However, the elongated member 12 may be other shapes. For example, the cross section of the elongated member taken along a plane perpendicular to the center line CL of the elongated member may be oval, elliptical, octagonal or square, for example.

The elongated member 12 of the illustrated directional drug delivery stent 11 also has a fluid opening or delivery means for directionally delivering a biologically active agent within the cavity or interior 20. As illustrated in FIGS. 1 and 2, the fluid opening or delivery means may be a slit shaped opening 22 extending along the outer surface 16 of the stent which allows the active agent to be delivered from the cavity 20. Although the slit shaped opening 22 is illustrated, any number of fluid opening configurations may be fashioned. For example, a series or plurality of holes, grooves, small indentations, and intermittent recessions could all be fluid openings and delivery means for directionally delivering the biologically active agent. Furthermore, the opening 22 need not extend the entire length of the elongated member 12. For example, the delivery means 22 may be located intermittently along the length of the tubular member 12.

As illustrated in FIG. 2, the stent 11, according to one embodiment of the present invention, may be positioned in a body lumen 13, such as a blood vessel, bronchial passageway, intestine, the rumen of an animal, nasal cavity, cervical area, or ear, for example. The drug delivery stent 11 illustrated in FIGS. 1 and 2 has an outer surface 16 having a luminal portion 18 for contacting the interior of the body lumen, which may include a luminal fluid, bodily liquid, gas, air, or any other substance that may be within the body lumen. The outer surface 16 also has a support portion 19 for supporting the walls 14 of the body lumen 13, which may be an exemplary blood vessel. The location of the slit shaped opening 22 along the outer surface 16 of the stent 11 provides directional drug delivery of the active agent from the cavity or interior 20. For example, in the embodiment of the present invention illustrated in FIG. 2, the delivery means, fluid opening, or exemplary slit 22 is positioned such that the active agent is delivered directly to the wall 14 of the body lumen 13. Because the slit 22 of the embodiment of the present invention illustrated in FIG. 2 directionally delivers the biologically active agent from the cavity 20 only through the support portion 19, the active agent is not directed into the interior of the body lumen, but is instead delivered to the walls 14. Thus, the fluid opening, or slit opening 22 in FIGS. 1 and 2 is only in a portion of the circumference of the outer surface 16 of the tubular member 12, permitting the biologically active agent 23 in the interior or cavity 20 to be directionally delivered exteriorly of the elongated member at a predetermined location, which in the embodiment illustrated in FIG. 2, is the wall 14. This is particularly advantageous when the drug delivery stent illustrated in FIG. 2 is used in a blood vessel; because the slit opening 22 of the embodiment of the present invention illustrated in FIG. 2 is located at the support portion 19, the blood stream of a blood vessel is only exposed to the smooth and luminal portion 18 of the stent 11, minimizing the possibility of thrombosis after the stent is expanded within the blood vessel.

Although the directional drug delivery stent 11 illustrated in FIG. 2 includes a fluid opening 22 located at the support portion 19 of the elongated member 12 such that the wall 14 immediately adjacent the fluid opening is the predetermined location where directional drug delivery occurs, other predetermined locations are possible. Generally speaking, the delivery means or fluid opening 22 is only in a portion of the circumference of the elongated or tubular member 12; the circumference is the perimeter, periphery or boundary line of the cross sectional area of the elongated or tubular member taken along the plane perpendicular to the center line CL of the elongated member. Thus, because the delivery means is only in a portion of the circumference of the elongated member, the biologically active agent located within the cavity or interior 20 is delivered exteriorly of the elongated member through the delivery means or fluid opening at a predetermined location. Directionally delivery occurs over less than the entire circumferential extent such that the biologically active agent is delivered to a predetermined location.

The elongated member 12 is preferably formed of a fairly rigid, impermeable, and strong material which is non-biodegradable. The elongated member material is preferably a biocompatible metal or alloy such as stainless steel, titanium, platinum, tantalum, silver, tungsten, gold, and their alloys as well as gold-plated ferrous alloys, platinum-plated ferrous alloys, cobalt-chromium alloys and titanium nitride coated stainless steel. Alternatively, the elongated or tubular member 12 may be formed of a polymer, such as polyether sulfone, polyamide, polycarbonate, polypropylene, high molecular weight polyethylene, carbon fiber, and the like. The elongated member 12 may also be formed of semipermeable or micro-porous material.

The helical stent 11 according to one embodiment of the present invention used in blood vessels has an initial diameter at which it is inserted into a body lumen, and an expanded final diameter. For many such applications, the initial diameter of the stent 11 will be in the range of from about 1.25 mm to 2 mm and the expanded final diameter will be from about 2 mm to about 6 mm. The stent 11 desirably has the property such that it retains its shape after expansion by a balloon catheter or other method.

Although the stent 11 formed from the elongated member 12 illustrated in FIG. 1 has a helical or coil shape, the present invention relates to stents having other configurations such as coiling stents, expandable tube stents, roving wire stents, and wire mesh stents. Thus, the elongated member 12 may be the filaments or fibers which form a mesh stent. In such alternative stent configuration, the directional drug delivery stent according to the present invention, like the stent 11 illustrated in FIGS. 1 and 2, will have a longitudinal axis or longitudinal center axis L, which is, generally, an imaginary substantially straight line running the longer direction of the stent and about which the body of the stent is symmetrically arranged. The center axis or the center line CL of the tubular or elongated member 12 of the directional drug delivery stent according to the present invention will not be coincident with the longitudinal axis or the longitudinal center axis L of the stent. In other words, the center line CL of the elongated member 12 is located radially spaced from the longitudinal center axis L of the stent 11.

The tubular member 12 of the stent 11 is formed of a material which is not biodegradable, bioerodible, or resorbable and remains in the body lumen to prevent collapse of the body lumen walls even after the active agent 23 has been completely diffused from the cavity. The stent 11 functions both to physically support the body lumen wall and also to prevent restenosis and thrombosis by directionally delivering the active agent 23 to a predetermined location, such as a body lumen wall or a luminal fluid. Thus, the stent 11 according to one embodiment of the present invention prevents restenosis, thrombosis, and collapse of the blood vessel more completely than the prior art stents which do not provide both physical support of the blood vessel without exposure to a thrombogenic surface, and delivery of an active agent directly to the vessel walls. Furthermore, by delivering the active agent directly to the vessel walls, more efficient use of the active agent is possible and there is no exposure of thrombogenic polymers or agents to the blood vessel.

Figure 3:
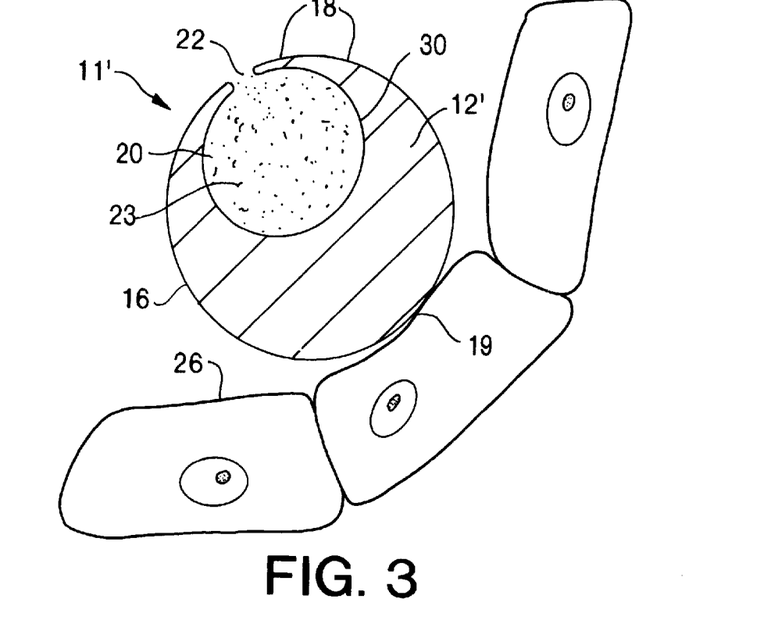
FIG. 3 is an enlarged cross-sectional view of the elongated member of a stent according to the present invention positioned in a body lumen.

An enlarged cross-sectional view of the elongated member 12' of the stent 11', according to one embodiment of the present invention positioned in a body lumen is illustrated in FIG. 3. As shown in FIG. 3, the elongated member 12' of the stent 11' has an interior or cavity 20, which in the illustrated embodiment is a concave shaped groove. The cavity 20 illustrated in FIG. 2 is formed by the surface 30. In the case of a helical stent 11', the cavity 20 and the slit shaped opening 22 extend along the helical path of the elongated member 12'. In the embodiment of the present invention illustrated in FIG. 3, the depth of the cavity 20 within the stent 11' is no more than half the cross section diameter of the elongated member 12', although any depth may be used which still allows the stent 11' to structurally support the lumen walls.

The cavity 20 of the embodiment of the present invention illustrated in FIG. 3 has an elongated or oval cross-sectional shape with the elongated side of the oval at the outer surface 16 of the tubular member 12'. However, the size and shape of the interior or cavity 20 can be any number of shapes and still be within the confines of the present invention. Furthermore, the size and shape of the cavity 20 may be varied to control the total amount of active agent 23 which is delivered and the rate of delivery. The size of the delivery means or fluid opening, which is a slit shaped opening 22 in the embodiment of the present invention illustrated in FIG. 3 can also be varied to control the rate of delivery of the active agent 23. The width of the slit shaped opening 22 of the embodiment of the present invention illustrated in FIGS. 1, 2 and 3 is between 0.1 and 49%, preferably between 10 and 25%, of the circumference of the elongated member 12 and 12'.

The embodiment of the present invention illustrated in FIG. 3 directionally delivers the biologically active agent 23 into the interior of the body lumen, which may include a fluid, gas, or other bodily substance. The delivery means, or the slit opening 22 has a width as described above, and permits directional delivery of the biologically active agent 23 from the cavity 20 through only the luminal portion 18 of the outer surface 16 of the elongated member 12'. The biologically active agent 23 is not directionally delivered to the wall 26 of the body lumen in the embodiment of the present invention illustrated in FIG. 3. Thus, the present invention permits directional delivery to a predetermined location, which in FIG. 3 is the interior of the body lumen or a luminal fluid located therein, by providing at least one fluid opening in only a portion of the circumference of the tubular member.

Figure 4:
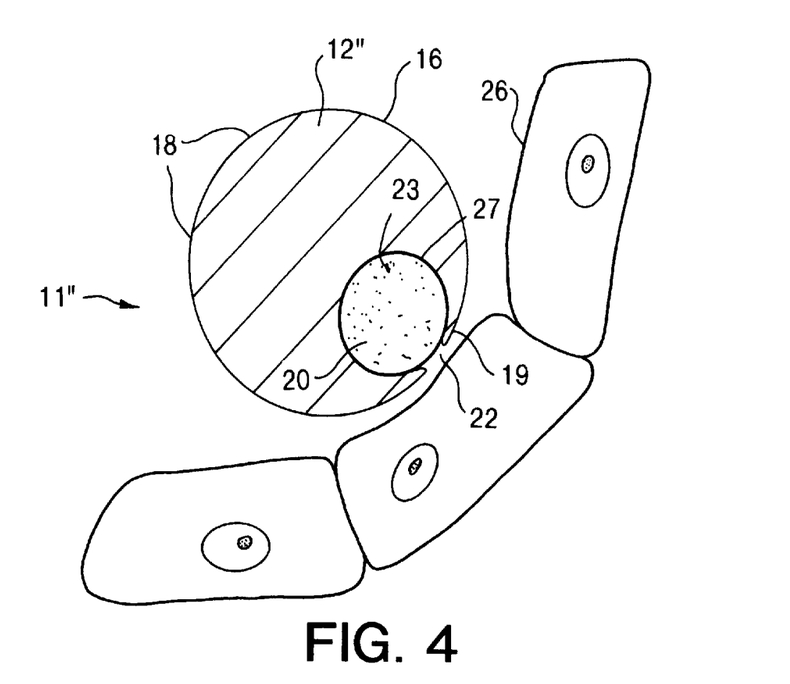
FIG. 4 is an enlarged cross-sectional view of the elongated member of an alternative embodiment of a stent according to the present invention positioned in a body lumen.

FIG. 4, like FIG. 2, illustrates a stent 11" according to another embodiment of the present invention which directionally delivers the biologically active agent 23 from the cavity 20 and through the slit opening 22, which is located at the support portion 19 of the outer surface 16, such that the biologically active agent is delivered to the body lumen wall 26.

As illustrated in the embodiment of the present invention shown in FIG. 4, the cavity 20 preferably contains a biocompatible delivery matrix 27 containing a biologically active agent for release. Such an exemplary delivery matrix 27 may be a biodegradable or non-biodegradable material. Examples of biocompatible polymeric matrix 27 formulations which may be disposed within the cavity 20 and incorporate the active agents 23 are polymers such as poly-ethylene-vinyl acetate, polyethylene, polyesters, poly anhydrides, polyorthoesters, polyamides, polyethers, and polyurethanes. Other delivery matrix 27 compounds such as waxes, fats or other biocompatible materials may also hold the biologically active agents 23. However, as illustrated in FIG. 3, no delivery matrix 27 is needed, especially if the biologically agent 23 has a sufficiently low solubility, permitting controlled diffusional delivery of the agent.

Figure 5:
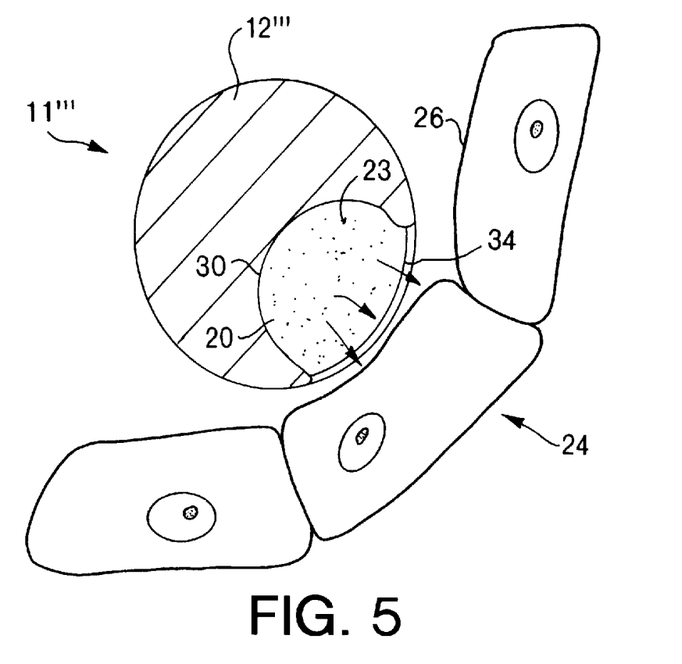
FIG. 5 is an enlarged cross-sectional view of the elongated member of an alternative embodiment of a stent according to the present invention positioned in a body lumen.

As depicted in FIG. 5, the elongated member 12''' of the stent 11''', according to another embodiment of the present invention may also optionally include delivery means having a membrane 34 which covers the slit shaped opening and allows the active agent to diffuse through the membrane to the desired predetermined location. The membrane 34 may be selected to provide a desired diffusional delivery rate of the active agent 23. Suitable membranes 34 for use in the present invention to control the delivery of the active agent 23 include, but are not limited to, poly-ethylene-vinyl acetate, polyethylene, polyesters, polyanhydrides, polyorthoesters, polyamides, polyethers, and polyurethanes.

Figure 6:
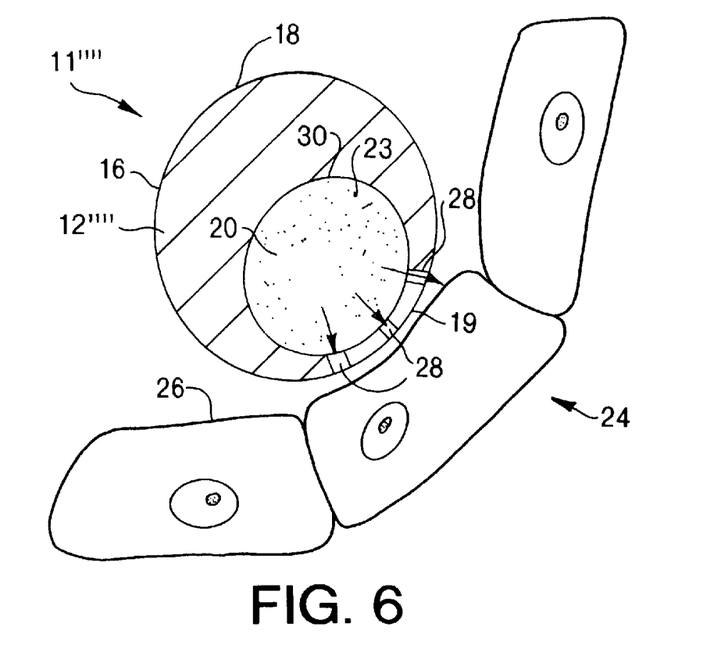
FIG. 6 is an enlarged cross-sectional view of the elongated member of an alternative embodiment of a stent according to the present invention positioned in a body lumen.

According to an alternative embodiment of the present invention which is illustrated in FIG. 6, the tubular member 12'''' of the stent 11'''', is provided with a plurality of fluid openings or holes 28 in only a portion of the circumference of the elongated member which are the delivery means for directionally delivering the biologically active agent 23. Directional delivery of the active agent is provided from the cavity 20 through the plurality of holes 28 to the lumen walls 26. The size and number of the holes 28 may be varied to control the rate of delivery of the active agent from the stent 11''''. The holes 28 occupy between 0.1 and 49%, preferably between 10 and 25% of the circumference of the tubular or elongated member 12''''.

Figure 7:
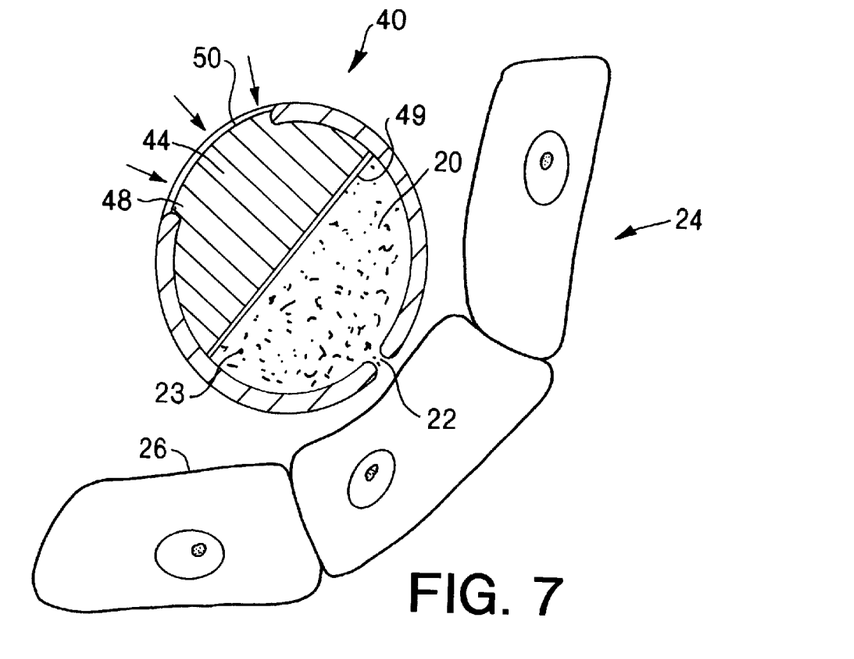
FIG. 7 is an enlarged cross-sectional view of the elongated member an osmotic directional delivery stent according to the present invention positioned in a body lumen.

A further aspect of the present invention relates to an osmotic directional delivery stent 40 illustrated in FIG. 7. According to the osmotic delivery version, the tubular member of the stent 40 includes an interior or cavity 20 having a biologically active agent 23 as in the embodiment of FIGS. 3–6. However, the stent 40 also includes a fluid-imbibing osmotic agent 44 which is adjacent the biologically active agent 23.

As shown in FIG. 7, the tubular member of the stent 40 is provided with a fluid inlet opening 48 which allows fluid from, for example, the interior of the body lumen 24 to enter the osmotic agent 44 causing it to swell. The osmotic agent 44 may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species. Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000, poly(vinylpyrrolidone) with molecular weight of 10,000 to 360,000, anionic and cationic hydrogels, poly-electrolyte complexes, poly(vinyl alcohol) having low acetate residual, optionally cross linked with glyoxal, formaldehyde or glutaraldehyde and having a degree of polymerization of 200 to 30,000, a mixture of methyl cellulose, cross linked agar and carboxymethyl cellulose, a mixture of hydroxypropyl methycellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross linked indene-maleic anhydride polymers, Good-Rite polyacrylic acids having molecular weights of 80,000 to 200,000, Polyox polyethylene oxide polymers having molecular weights of 100,000 to 5,000,000, starch graft copolymers, and Aqua-Keeps acrylate polymer polysaccharides, inorganic salts, organic salts, sugars, polysaccharides, polymeric hydrogels, or amphoteric molecules.

The osmotic agent 44 operates by imbibing fluid from the biological environment of use 24 and causes the osmotic agent to expand in a controlled manner. The expanding osmotic agent 44 compresses the active agent 23 within the cavity 20 causing the active agent to be released in a controlled manner through the slit shaped opening 22 to a predetermined location, which in the embodiment illustrated in FIG. 7 is the wall 26 of the luminal body 24. The fluid inlet opening 48 may also be located at the wall of the vessel, while the slit shaped opening 22 may be directed at the interior of the luminal body.

The size of the fluid inlet opening 48 may be varied to regulate the delivery rate of the active agent 23 by controlling the rate at which the fluid enters and swells the osmotic agent 44. If the stent 40 is made of a semipermeable micro-porous material, no fluid inlet opening 48 is needed. The fluid inlet opening 48 to the cavity 20 may also be covered with a membrane 50 which controls the rate of delivery of the active agent by controlling the rate at which fluid from the body lumen 24 enters the osmotic agent 44.

The embodiment of the present invention illustrated in FIG. 7 also includes an optional separating member 49 between the osmotic agent 44 and the biologically active agent 23. The optional separating member 49 keeps the osmotic agent 44 separate from the biologically active agent 23 while also allowing the osmotic agent to swell. The separating member 49 may move within the cavity or interior 20, or the separating member may be fixed within the cavity and made of a flexible material that stretches as the osmotic agent imbibes fluid from the biological environment of use. However, the separating member 49 is not required, and there may be only an interface between the osmotic agent 44 and the biologically active agent 23.

Figure 8:
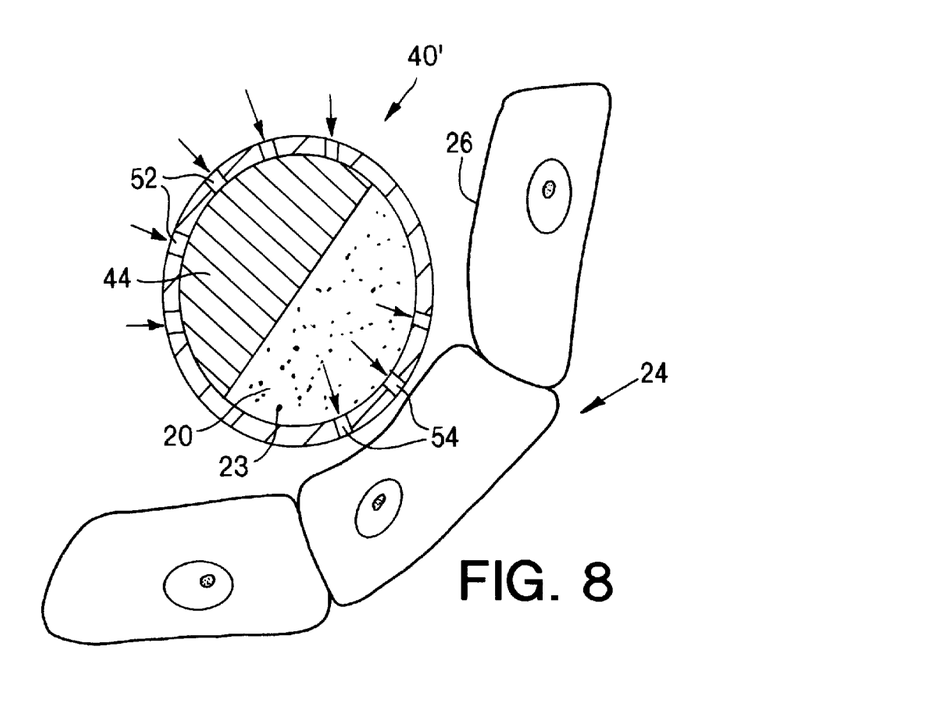
FIG. 8 is an enlarged cross-sectional view of the elongated member of an alternative embodiment of an osmotic directional delivery stent according to the present invention positioned in a body lumen.

FIG. 8 illustrates an alternative embodiment of the osmotic delivery stent 40 ' in which a plurality of fluid inlet openings 52 are provided in the tubular member for allowing fluid to enter and swell the osmotic agent 44 in the cavity 20. A plurality of holes 54 located in only a portion of the circumference of the tubular member are the delivery means or fluid openings for directionally delivering the active agent 23 from the cavity 20 to the wall 26 of the body lumen 24. The number and size of the openings 52, 54 may be varied to regulate the delivery rate of the active agent 23.

Figure 9:
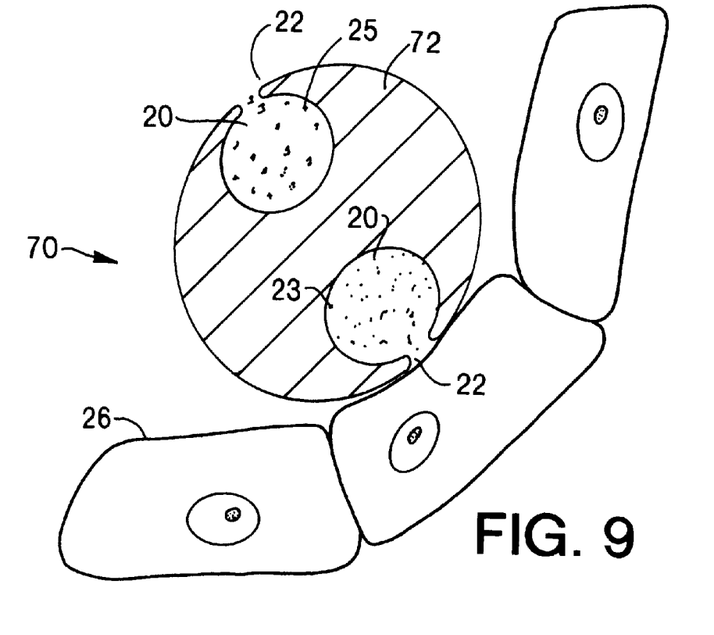
FIG. 9 is an enlarged cross-sectional view of the elongated member of an alternative embodiment of a multi-directional delivery stent according to the present invention positioned in a body lumen.

FIG. 9 illustrates an alternative embodiment of a multi-directional delivery stent 70 according to the present invention in which the elongated or tubular member 72 includes two cavities or interiors 20. Each of the two cavities contains a biologically active agent 23, 25 for directional delivery to two different predetermined locations. In this embodiment, the first biologically active agent 23 is directionally delivered to the wall 26 through the slit shaped opening 22 located in only a portion of the circumference of the elongated member, while the second biologically active agent 25 is located in the other of the two cavities 20 and is also directionally delivered to a predetermined location, which in this embodiment, is the interior of the body lumen. The first and second biologically active agents 23, 25 may be the same agent or different agents for different treatments.

Figure 10:
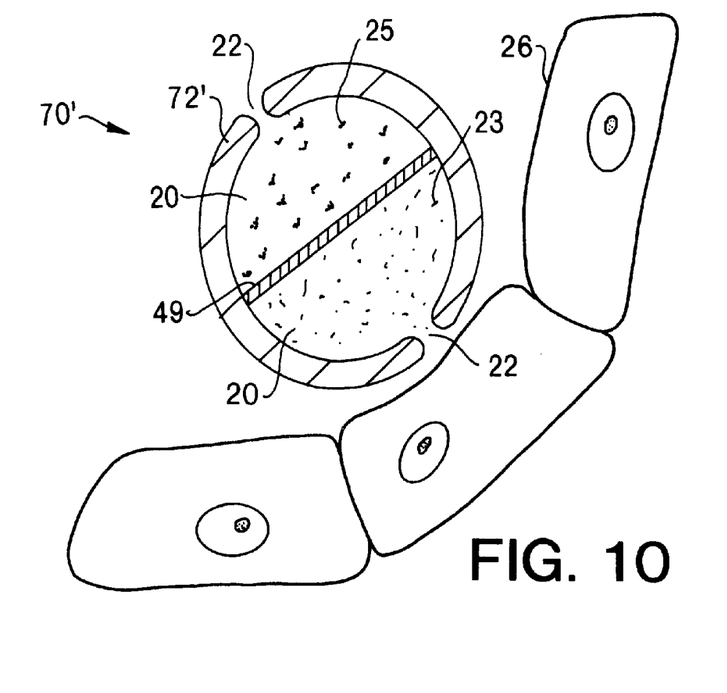
FIG. 10 is an enlarged cross-sectional view of the elongated member of an alternative embodiment of a multi-directional delivery stent according to the present invention positioned in a body lumen.

FIG. 10 illustrates an alternative embodiment of the multi-directional delivery stent 70' according to the present invention in which the elongated or tubular member 72' includes one cavity 20 for containing a first biologically active agent 23 and a second biologically active agent 25. The cavity 20 of the tubular member 12 includes a separating member 49 located between the biologically active agents 23, 25. The separating member 49 may be a structural support maintaining the structural integrity of the elongated member 72', and/or a device, such as one of the above described membranes, for separating the two agents 23, 25 from each other within the cavity 20. However, the separating member 49 is not required, leaving only an interface between the two agents 23, 25; in such an embodiment, to maintain structural integrity of the tubular member 12 and stent 70', the slit shaped openings 22 would not run the entire length of the elongated member. Thus, the embodiment of the present invention illustrated in FIG. 10 includes two means or openings 22 located in only a portion of the circumference of the tubular member for delivering two biologically active agents 23, 25 from one cavity 20 to two different predetermined locations.

Figure 11:
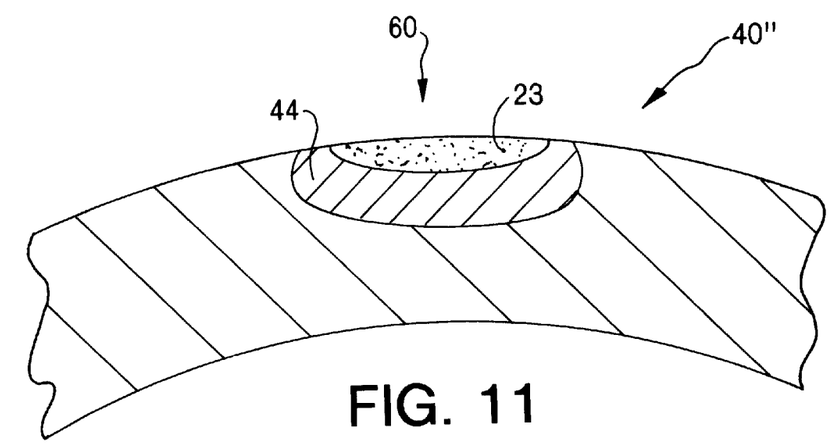
FIG. 11 is an enlarged cross-sectional side view of the elongated member of an alternative embodiment of an osmotic directional delivery stent according to the present invention.

FIG. 11 illustrates a longitudinal cross sectional view of another alternative embodiment of an osmotic delivery stent 40" according to the present invention. The stent 40" includes an osmotic engine assembly 60. The osmotic engine assembly 60 may be fashioned separately in the shape of a tablet or capsule and inserted into the interior or cavity of the stent 40". The osmotic engine assembly 60 includes the osmotic engine 44 and the biologically active agent 23. The osmotic agent and/or the biologically active agent 23 may be optionally coated with a semipermeable membrane. Once the assembly 60 is positioned within the cavity, the oval shaped opening through which the osmotic engine 60 was inserted, permits both the fluid from the biological environment of use to enter the osmotic agent 44 and the biologically active agent 23 to exit the stent at the predetermined location.

Figure 12:
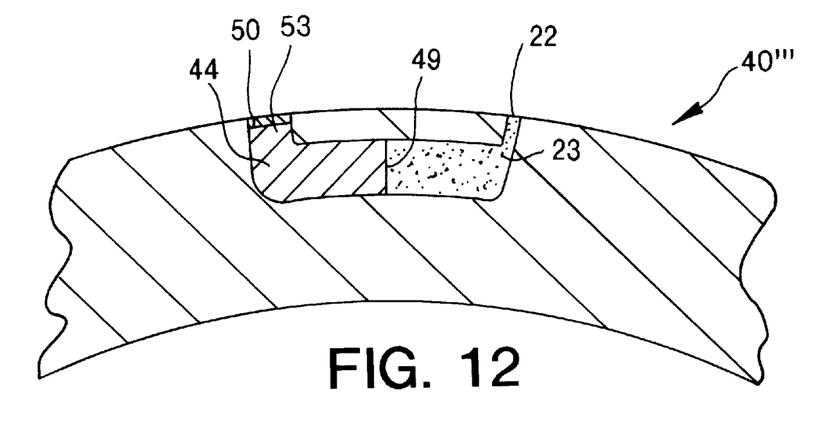
FIG. 12 is an enlarged cross-sectional side view of the elongated member of an alternative embodiment of an osmotic directional delivery stent according to the present invention.

FIG. 12 illustrates a longitudinal cross sectional view of another alternative embodiment of an osmotic delivery stent 40''' according to the present invention. The stent 40''' includes delivery means or fluid opening 22 through which the biologically active agent 23 is directionally delivered. The interior or cavity is shaped like a channel within the stent body and holds an osmotic agent 44 adjacent to the biologically active agent 23. This embodiment of the present invention may optionally include a separating member 49 between the osmotic agent 44 and the biologically active agent 23, and a semipermeable membrane 50 located at the fluid inlet opening 53.

Figure 16:
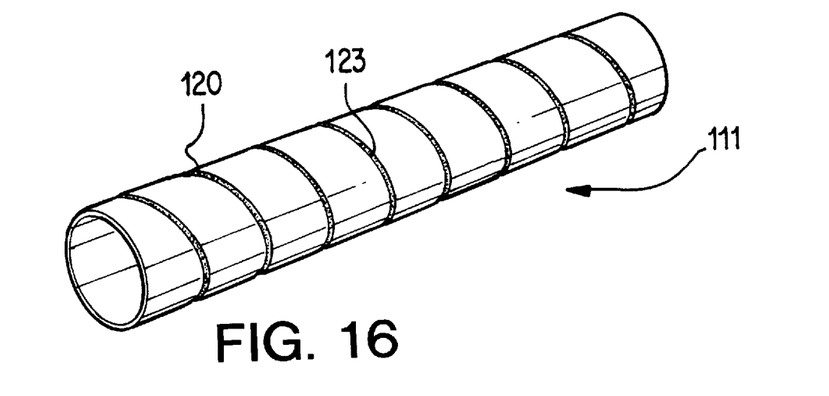
FIG. 16 is a perspective view of a grooved tube of FIG. 15, where only the groove contains an active agent.
Figure 17:
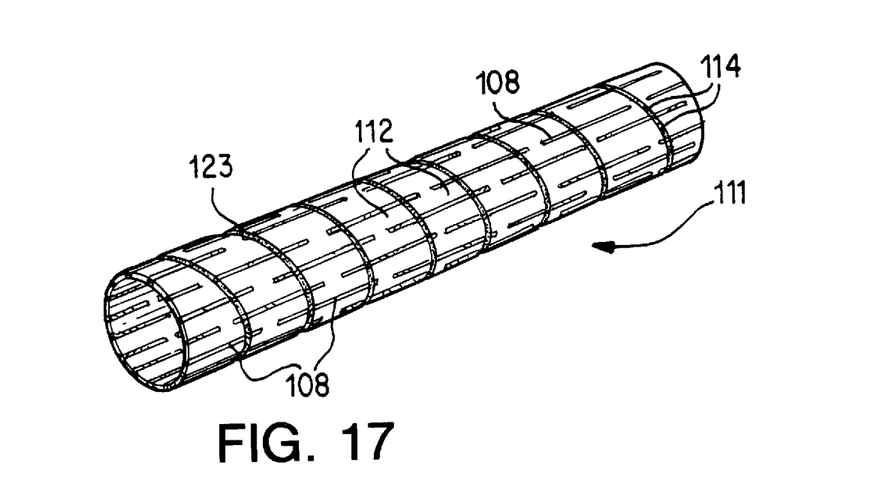
FIG. 17 is a perspective view of a grooved tube of FIG. 16 with a plurality of slots formed therein.
Figure 18:
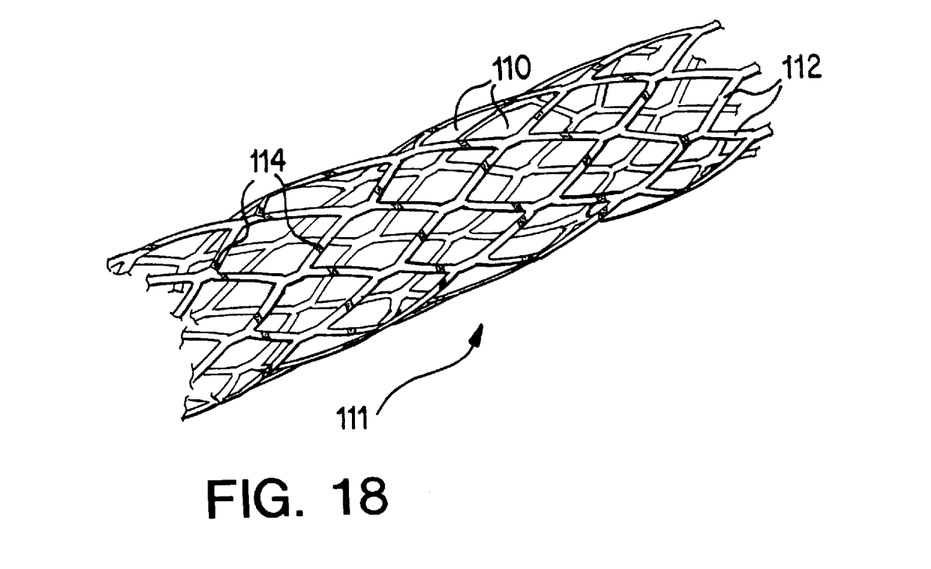
FIG. 18 is a perspective view of an expanded stent according to an embodiment of the present invention obtained from the grooved tube of FIG. 17.

FIG. 17 illustrates an example of the aforementioned expandable tube-type stent 111 according to another embodiment of the present invention. FIG. 18 illustrates the stent 11 in an expanded state. FIGS. 13–17 illustrate one preferred method of making the stent 111.

Figure 13:
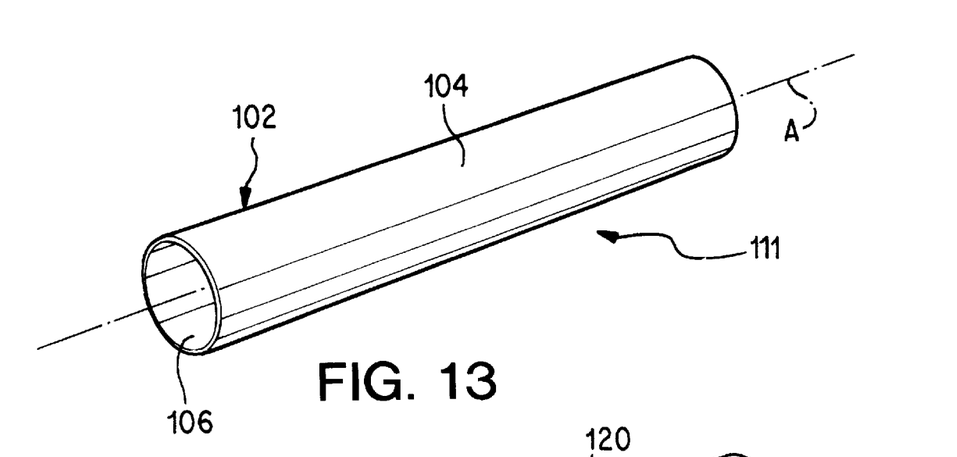
FIG. 13 is perspective view of a tube that is a precursor of a stent according to an embodiment of the present invention.

The expanded tube-type stent 111 is manufactured by cutting an elongated tubular member into tubular sections, one of which is shown in FIG. 13. The tubular member may be manufactured from any of the nonbiodegradable materials described above in reference to the other embodiments of stents according to the present invention. For example, the tubular member may be made from titanium, stainless steel, nitinol, tantalum, or other similar materials. Although other configurations of the tubular member are contemplated, as FIG. 13 illustrates, the section of tubular member is preferably a cylindrical tube 102 having a longitudinal center axis A coincident with the longitudinal center axis of the finished stent 111.

Figures 14, 14A:
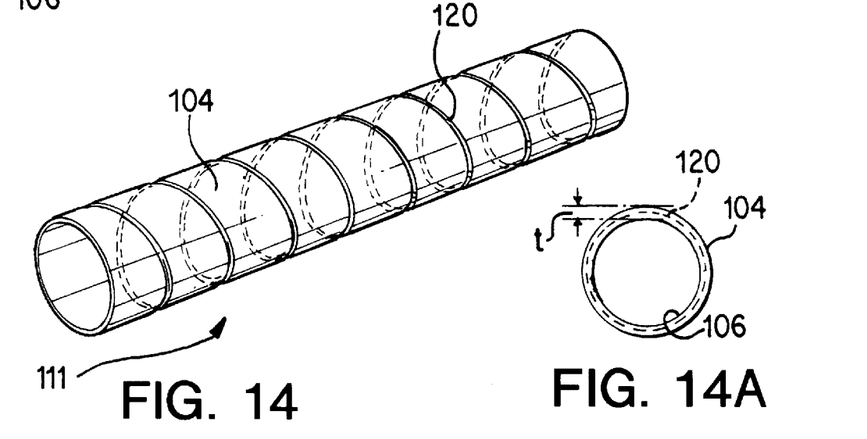
FIG. 14 is a perspective view of a tube of FIG. 13 with a groove.
FIG. 14A is an end view of the tube of FIG. 14.
Figure 15:
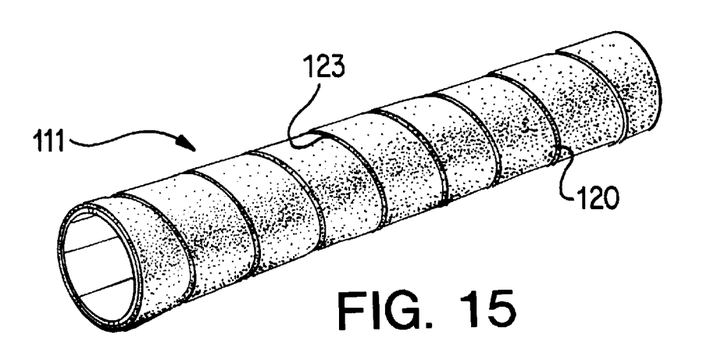
FIG. 15 is a perspective view of a grooved tube of FIGS. 14 and 14A, where the grooved tube is coated with an active agent.

A recessed active agent receiving portion or groove 120 is formed in the exterior surface 104 of the tube 102. The groove 120, illustrated in FIG. 14, is preferably a continuous helical or coiling groove extending around the tube 102, although other configurations are contemplated such as straight, parallel, and zig-zagging grooves. In addition, the groove 120 need not be continuous. For example, a plurality of spaced apart grooves may be formed in the exterior surface 104 of the tube 102. The groove 120 may be formed by methods well known in the art, but is preferably formed with a laser to define a groove having a concave shape when viewed in cross-section. As shown in FIG. 14A, the groove 120 does not extend through the wall thickness t of the tube 102. In other words, the groove 120 does not completely pierce through the interior surface 106 of the tube 102, and so the depth of the groove is less than the wall thickness t (i.e., the tubular member thickness measured between the exterior surface 104 and the interior surface 106). Similar to the previously described embodiments, the recessed active agent receiving portion or groove 120 defines a fluid opening through which an active agent 123 may be directionally delivered.

After the groove 120 has been formed in the exterior surface 104 of the tube 102, the tube is coated with an active agent 123, such as those described above. The active agent 123 may be applied to the exterior surface 104 by spraying the tube 102, dipping the tube, or by other conventional methods. Because at least the entire exterior of the tube is coated, the groove 120 is also filled with the active agent 123. In the embodiment illustrated in FIG. 15, the exterior surface 104 is covered and the helical groove 120 is filled with a biocompatible delivery matrix containing a biologically active agent for release, similar to the stent 11" illustrated in FIG. 4.

After the tube 120 is coated with the active agent 123, the excess biological active agent is preferably removed from the exterior surface of the tube 102. As shown in FIG. 16, this step of the manufacturing process of the stent 111 removes all active agent from the tube 102 except for the active agent in the groove 120. The excess active agent may be removed, for example, by wiping the tube 102, passing the tube through a tight fitting sleeve or collar, or scraping the tube. As a result of this step, the active agent 123 is only contained in the groove 120. Alternatively, the active agent 123 may be left on the exterior surface 104 of the tube 102, or the groove 120 may be directly filled with the active agent 123 without coating the entire exterior surface of the tube.

Once the recessed active agent receiving portion or groove 120 has been filled with active agent 123 such that it contains the active agent, a plurality of perforations, slits, or slots 108 are formed in the tube 102, as illustrated in FIG. 17. The slots 108 are formed in the exterior surface 104 of the tube 102, and extend completely through the tubular member thickness or wall thickness t. The slots 108 are preferably formed with a laser or other conventional apparatus. The through slots 108 shown in FIG. 17 are parallel and staggered, but may be any conventional configuration, so long as they permit the stent 111 to be expanded. For example, the slot 108 may extend straight along the entire length of the tube 102 such that the stent is split and coils upon itself like a wood shaving, or may helically extend around the tube such that the stent is shaped like a coil spring. Thus, it is apparent that at least one function of the slots is to permit the stent 111 to be expanded, such as illustrated in FIG. 18, although, as described above in regard to other embodiments of the present invention, such slots may not be necessary for the stent to be expandable.

Because the preferred slots 108 extend longitudinally along the tube 102 and the preferred recessed active agent receiving portion or groove 120 extends helically around the tubular member, the slots intersect the groove to define a plurality of spaced apart groove portions 114, each containing the active agent 123. The spaced apart groove portions 114 are positioned relative to one another such that together they define or outline a helical shape, as shown in FIG. 17.

Once the slots 108 have been formed in the tube 102, it is apparent that the tube is expandable as shown in FIG. 18. When the tube is expanded, the tubular material between the slots 108 forms the angled fibers or elongated members 112, and the slots 108 form the interstitial openings 110. Thus, as shown in FIG. 17, the slots 108 in the unexpanded stent 111 define a plurality of parallel elongated members 112. At least some of the elongated members 112 contain groove portions 114 or cavities in which the active agent is located. Hence, those portions of the elongated members 112 that contain groove portions 114 have an active agent delivery opening in only a portion of the circumference of the elongated member for directional delivery of the active agent 123 contained in the groove portion, similar to the previously described embodiments of the present invention. Because the slots 108 are formed with a laser, the elongated portions 112 tend to have a square or rectangular cross-sectional shape. Other conventional slot forming processes may form other cross sectional shapes of the elongated members 112. As is apparent from FIGS. 17 and 18, the individual fibers or elongated members 112 each have a longitudinal axis or center line that is located radially spaced from the longitudinal center axis of the stent 111.

Like the previously described embodiments of stents according to the present invention, the tube 102 of the stent 111 is formed of a material which is not biodegradable, bioerodible, or resorbable and remains in the body lumen to prevent collapse of the body lumen walls even after the active agent 123 has been completely diffused from the cavity. The stent 111 functions both to physically support the body lumen wall and also to prevent restenosis and thrombosis by directionally delivering the active agent 123 to a predetermined location, such as a body lumen wall or a luminal fluid. Thus, the stent 111 can prevents restenosis, thrombosis, and collapse of the blood vessel more completely than the prior art stents which do not provide both physical support of the blood vessel without exposure to a thrombogenic surface, and delivery of an active agent directly to the vessel walls. Furthermore, by delivering the active agent 123 directly to the vessel walls, more efficient use of the active agent is possible and there is no exposure of thrombogenic polymers or agents to the blood vessel.

While the invention has been described in detail with reference to preferred embodiments thereof, it will be apparent to one skilled in the art that various changes can be made, and equivalents employed without departing from the spirit and scope of the invention.

We claim:

1. A nonbiodegradable and expandable stent for directionally delivering an active agent, the stent comprising:
   a nonbiodegradable tubular member having an exterior surface and an interior surface together defining a tubular member thickness of said tubular member, said tubular member having a recessed active agent receiving portion formed in said exterior surface, said recessed active agent receiving portion having a depth less than said tubular member thickness, said recessed active agent receiving portion containing at least one active agent.

2. The stent according to claim 1, wherein said recessed active agent receiving portion is a helical groove extending around said tubular member.

3. The stent according to claim 1, further comprising a plurality of slots extending through said tubular member thickness, said recessed active agent receiving portion including a plurality of spaced apart groove portions, adjacent ones of said groove portions being separated by one of said slots.

4. The stent according to claim 3, wherein when said stent is expanded said slots expand to increase a distance between adjacent ones of groove portions.

5. The stent according to claim 1, wherein said tubular member is cylindrical.

6. The stent according to claim 1, wherein said active agent is contained in a delivery matrix.

7. An expandable stent for directionally delivering an active agent, the stent comprising:
   a nonbiodegradable and tubular member having an exterior surface and an interior surface together defining a tubular member thickness of said tubular member, said tubular member having a groove formed in said exterior surface, said groove having a depth less than said tubular member thickness, said groove containing at least one active agent.

8. The stent according to claim 7, wherein said groove is helical.

9. The stent according to claim 7, further comprising a plurality of slots extending through said tubular member thickness, said groove including a plurality of spaced apart groove portions, adjacent ones of said groove portions being separated by one of said slots.

10. The stent according to claim 9, wherein said slots extend parallel with a longitudinal axis of said tubular member.

11. The stent according to claim 9, wherein said slots are formed with a laser.

12. The stent according to claim 7, wherein said active agent is contained in a delivery matrix.

13. The stent according to claim 7, wherein said tubular member is pipe-shaped.

14. The stent according to claim 7, wherein said active agent is one of steroids, anti-inflammatory agents, restenosis preventing drugs, anti-thrombotic drugs, and tissue growth regulating drugs.

15. The stent according to claim 7, wherein said groove is formed with a laser.

16. An expandable stent for directionally delivering an active agent, the stent comprising:
   a nonbiodegradable and tubular member having an exterior surface and an interior surface together defining a tubular member thickness of said tubular member, said exterior surface of said tubular member having recessed means for receiving at least one active agent, said recessed means having a depth less than said tubular member thickness.

17. The stent according to claim 16, wherein said tubular member includes a plurality of openings passing through said tubular member thickness.

18. The stent according to claim 16, wherein said recessed means includes a helical groove formed in said exterior surface.

19. The stent according to claim 16, wherein said recessed means receives said at least one active agent.

20. The stent according to claim 19, wherein said active agent is contained in a delivery matrix.

21. The stent according to claim 19, wherein said recessed means includes a groove that is formed with a laser.

* * * * *